United States Patent [19]
Novak

[11] Patent Number: 6,012,922
[45] Date of Patent: Jan. 11, 2000

[54] AXIAL DISPLACEMENT BEARING CONNECTING A MULTI-SECTION SHAFT FOR QUICK REMOVAL OF DENTAL TOOLS FROM A HANDPIECE

[75] Inventor: Eugene J. Novak, Deerfield, Ill.

[73] Assignee: Tulsa Dental Products Inc., Des Plaines, Ill.

[21] Appl. No.: 09/148,091

[22] Filed: Sep. 4, 1998

Related U.S. Application Data

[60] Provisional application No. 60/058,123, Sep. 8, 1997.

[51] Int. Cl.[7] ................................. A61L 1/08; A61L 1/14
[52] U.S. Cl. ............................................ 433/126; 433/127
[58] Field of Search .................................. 433/126, 114, 433/127, 128

[56] References Cited

U.S. PATENT DOCUMENTS

| | | | |
|---|---|---|---|
| 302,430 | 7/1884 | Roque | 433/114 |
| 3,475,817 | 11/1969 | Loge | 433/126 |
| 3,631,597 | 1/1972 | Lieb et al. | 433/126 |
| 3,667,125 | 6/1972 | Seigneurin | 433/114 |
| 4,114,276 | 9/1978 | Malata et al. | 32/26 |
| 4,151,851 | 5/1979 | Bragg | 132/91 |
| 4,278,428 | 7/1981 | Straihammer et al. | 433/105 |
| 4,515,564 | 5/1985 | Lohn | 433/126 |
| 4,718,851 | 1/1988 | Kuhn | 433/122 |
| 4,753,595 | 6/1988 | Schuss et al. | 433/114 |
| 4,983,121 | 1/1991 | Straihammer et al. | 433/114 |
| 5,007,831 | 4/1991 | Bierbaum et al. | 433/114 |
| 5,062,796 | 11/1991 | Rosenberg | 433/82 |
| 5,267,860 | 12/1993 | Ingram, Jr. et al. | 433/116 |
| 5,275,558 | 1/1994 | Seney | 433/82 |
| 5,289,604 | 3/1994 | Kressner | 15/22.1 |
| 5,374,189 | 12/1994 | Mendoza | 433/125 |
| 5,482,462 | 1/1996 | Rosenstatter | 433/126 |
| 5,503,555 | 4/1996 | Bailey | 433/126 |
| 5,529,495 | 6/1996 | Edwards | 433/112 |
| 5,609,445 | 3/1997 | Dusing | 433/126 |

*Primary Examiner*—John J. Wilson
*Assistant Examiner*—Patrick A. Hilsmier
*Attorney, Agent, or Firm*—Douglas J. Hura; James B. Bieber

[57] ABSTRACT

A dental handpiece (10) is provided with a drive motor (13), a drive shaft (12) operatively affixed to the drive motor (13) at one end of the drive shaft (12). A dental tool (11) is operatively affixed at the other end of the drive shaft (12). The drive shaft (12) is journaled within a axial displacement bearing (60), such that manipulated rotation of the dental tool (11) causes a first drive shaft section (61) to be axially displaced from and relative to a second drive shaft section (62). The axial displacement bearing (60) is caused to contact a bearing (51) thereby causing the drive shaft (12) to bind due to the frictional forces generated by that contact. This allows sufficient force such that the dental tool 11 can be disengaged from the handpiece (10).

12 Claims, 5 Drawing Sheets

AXIAL DISPLACEMENT BEARING CONNECTING A MULTI-SECTION SHAFT FOR QUICK REMOVAL OF DENTAL TOOLS FROM A HANDPIECE

This application claims benefit of provisional application 60/058,123, filed Sep. 8, 1997.

TECHNICAL FIELD

The present invention generally relates to dental handpieces. More particularly, the invention relates to a dental handpiece that provides for the efficient securing and removing of a rotating dental tool therefrom. Specifically, the invention relates to a handpiece wherein a drive shaft is provided with an axial displacement-inducing bearing, such that manual rotation of the drive shaft causes separate sections thereof to be axially displaced, causing the shaft to physically contact and bind against journal bearings. This allows the user to manually exert a force upon the dental tool to remove it from the handpiece. The invention also provides an ergonomically profiled and textured gripping surface as well as a color coded, removable identifying device.

BACKGROUND OF THE INVENTION

Dental handpieces are known in the art for driving a number of dental tools such as prophy cups, abrading devices, polishing attachments and the like. Most often, a dental handpiece includes a rotating shaft within a housing and attached at one end to a drive motor and at the other end to the dental tool. As the motor causes the drive shaft to rotate, the drive shaft operates to cause the dental tool to rotate.

One common method of attaching the dental tool to the drive shaft is to use a threaded and rotatable coupling, wherein the drive shaft actually drives the coupling. The dental tool is threaded to the coupling and rotates therewith. For hygienic reasons, the dental tool is changed between patients and often, between procedures for a single patient. Therefore, efficient securing and removal of the dental tool is important to the overall efficiency of any given dental procedure.

While mating threads between the coupling device and the dental tool have proven to be efficient in securing the dental tool to the drive shaft, it has been found that removal of the tool from the threaded engagement is often difficult. The physical contact between the mating threads causes a friction fit between them which is often greater than whatever force is necessary to rotate the drive shaft. That is, when it is desired to remove the dental tool, the user will often grasp the tool and rotate it in a direction opposite that required to seat the tool. If the frictional forces between the mating threads are greater than that required to rotate the shaft, then the shaft will rotate and the threads will not disengage. This is often further complicated by the fact that the dental tool is often used with various viscous dental materials which can clog any spaces between the dental tool and the handpiece, making it more difficult to remove the dental tool.

It would not be an acceptable solution to make the force required to rotate the drive shaft greater, because the drive motor would then have to use greater force to rotate the drive shaft. This would serve to shorten the life of the motor.

Further, many low speed dental handpieces have both a forward and a reverse powered rotation function. It is possible to simply reverse the rotation of the drive motor to remove a dental tool. Such reversible motors and their associated control mechanisms, greatly inflate both the complexity and the expense of the handpiece.

For hygienic reasons, it would be desirable to differentiate between a plurality of different handpieces. The present invention provides for this need.

A need exists therefore, for a handpiece capable of permitting efficient securing and removal of a dental tool without the need for severely limiting the free rotation of the drive shaft. The handpiece should allow for such removal of the dental tool without the need for expensive and complex reversible motor capabilities. The handpiece should also allow for easy gripping and manipulation by the user.

SUMMARY OF THE INVENTION

It is therefore, an object of the invention to provide a dental handpiece for use in driving a rotatable dental tool.

It is another object of the invention to provide a dental handpiece as above, which will permit a dental tool to be efficiently secured thereto.

It is a further object of the invention to provide a handpiece as above, which will also provide for the efficient removal of the tool therefrom.

It is also another object of the invention to provide a handpiece which is easily grasped and manipulated in use.

It is a still further object of the invention to provide a dental handpiece which has an identifying indicia device, such that multiple handpieces can be distinguished.

These and other objects of the invention, which will become apparent from the following, are accomplished by the invention as herein described and claimed.

In general, a dental handpiece comprises a housing;
a head portion affixed to said housing;
a rotatable drive shaft journaled within said housing, and having a first and a second cooperating section and an axis of rotation;
a rotatable dental tool operatively connected to said first section of said drive shaft;
drive motor means operatively connected to said second section of said drive shaft to selectively and rotatably drive said drive shaft about its axis of rotation;
means to couple said first and second drive shaft sections, comprising an axial displacement bearing affixed to one of said sections and receiving the other said section;
said axial displacement bearing having at least one helical slot therein;
a pin means affixed to said shaft section received within said axial displacement bearing and said pin means positioned within said helical slot so as to be in operative, physical contact with said axial displacement bearing;
such that as said drive motor means causes said second section of said drive shaft to rotate, a rotating force is translated to said second section of said drive shaft by said pin being in said physical contact with said axial displacement bearing helical slot, thereby causing a rotational force to be applied to said dental tool and causing its rotation.

There is also provided according to the invention, a dental handpiece of the type having a drive motor unit rotatably driving a drive shaft journaled within a housing, and a dental tool affixed to said drive shaft, wherein rotation of said drive shaft causes said dental tool to rotate. The inventive handpiece is improved by having an indentation positioned upon the exterior surface of said housing; and, an identifying device positioned within said indentation and having a preselected color.

According to another aspect of the invention, a dental handpiece is provided of the type having a drive motor unit rotatably driving a drive shaft journaled within a housing portion of said handpiece, and a dental tool affixed to said drive shaft, wherein rotation of said drive shaft causes said dental tool to rotate; the improvement comprising:

said drive shaft comprising a first drive shaft section and a second drive shaft section; said dental tool operatively affixed to said first drive shaft section and said drive motor unit operatively affixed to said second drive shaft section; said second drive shaft section having an affixed bearing receiving at least a portion of said first drive shaft section; said bearing having at least one helical slot therein, said helical slot rising in the same direction as the normal operational direction of rotation as said drive shaft; a pin affixed to said first shaft section and positioned within said at least one helical slot; such that manipulation of said dental tool in its normal operational direction of movement causes said first drive shaft section to rotate in its normal operational direction of movement, thereby causing said pin to rise within said helical slot, causing the said first drive shaft section to be axially displaced from said second drive shaft section.

According to one configuration of the invention, a dental handpiece comprises a drive motor;

a drive shaft having a first and a second shaft section, said second shaft section operatively affixed to said drive motor;

a dental too operatively affixed at one end of said first shaft section;

said first shaft section being journaled within an axial displacement bearing means, such that manipulated rotation of said dental tool causes said first and second drive shaft sections to be axially displaced from one another.

PREFERRED EMBODIMENTS FOR CARRYING OUT THE INVENTION

Figure 3:
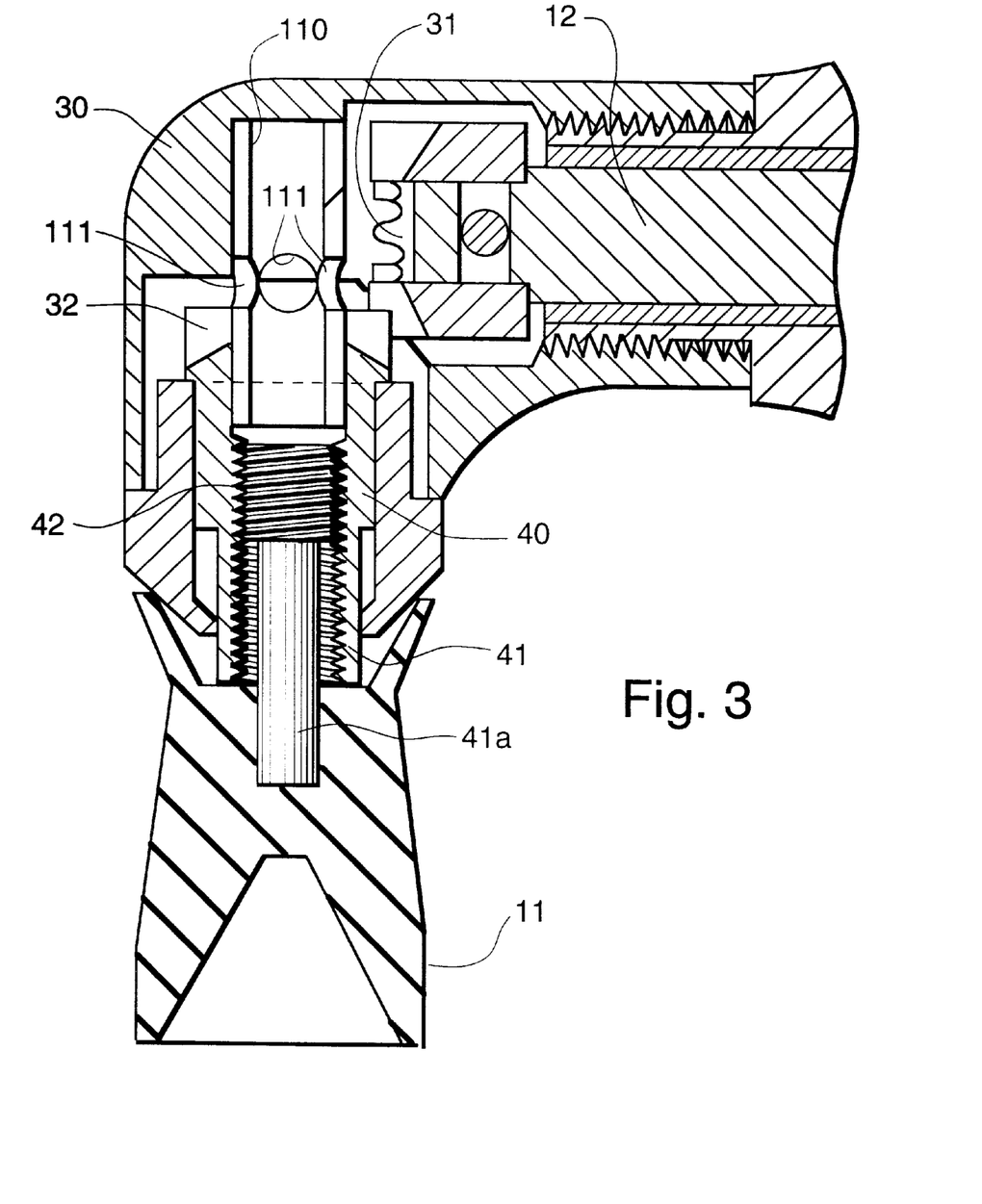
FIG. 3 is an enlargement of the area of FIG. 2 identified by the numeral 3.
Figure 5:
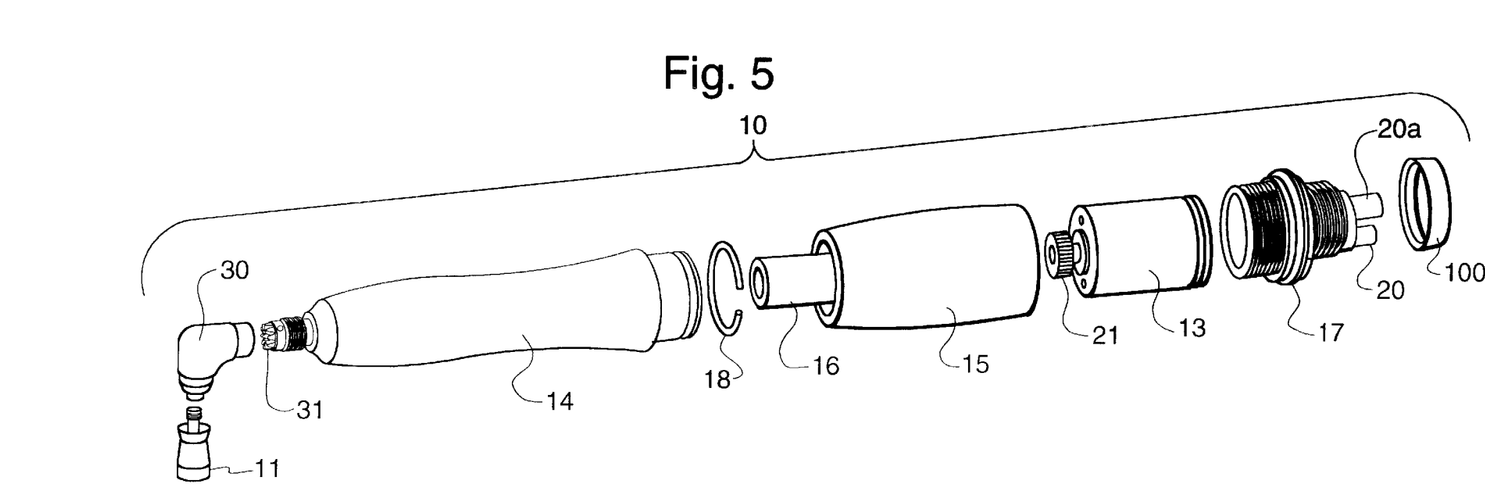
FIG. 5 is an exploded side view of the components of the handpiece of FIG. 1.

A handpiece according to the concepts of the present invention is generally designated by the number 10 on the attached drawings. Handpiece 10 is employed to operate a rotating dental tool such as rubber prophy cup dental tool 11 which is depicted for illustrative purposes. Handpiece 10 includes a rotating shaft 12 driven by a motor such as air drive motor 13 (FIGS. 3 and 5). Any conventional drive motor may be employed, although air motor 13 is preferred.

A housing 14 is provided within which drive shaft 12 is journaled as will be discussed below.

Figure 2:
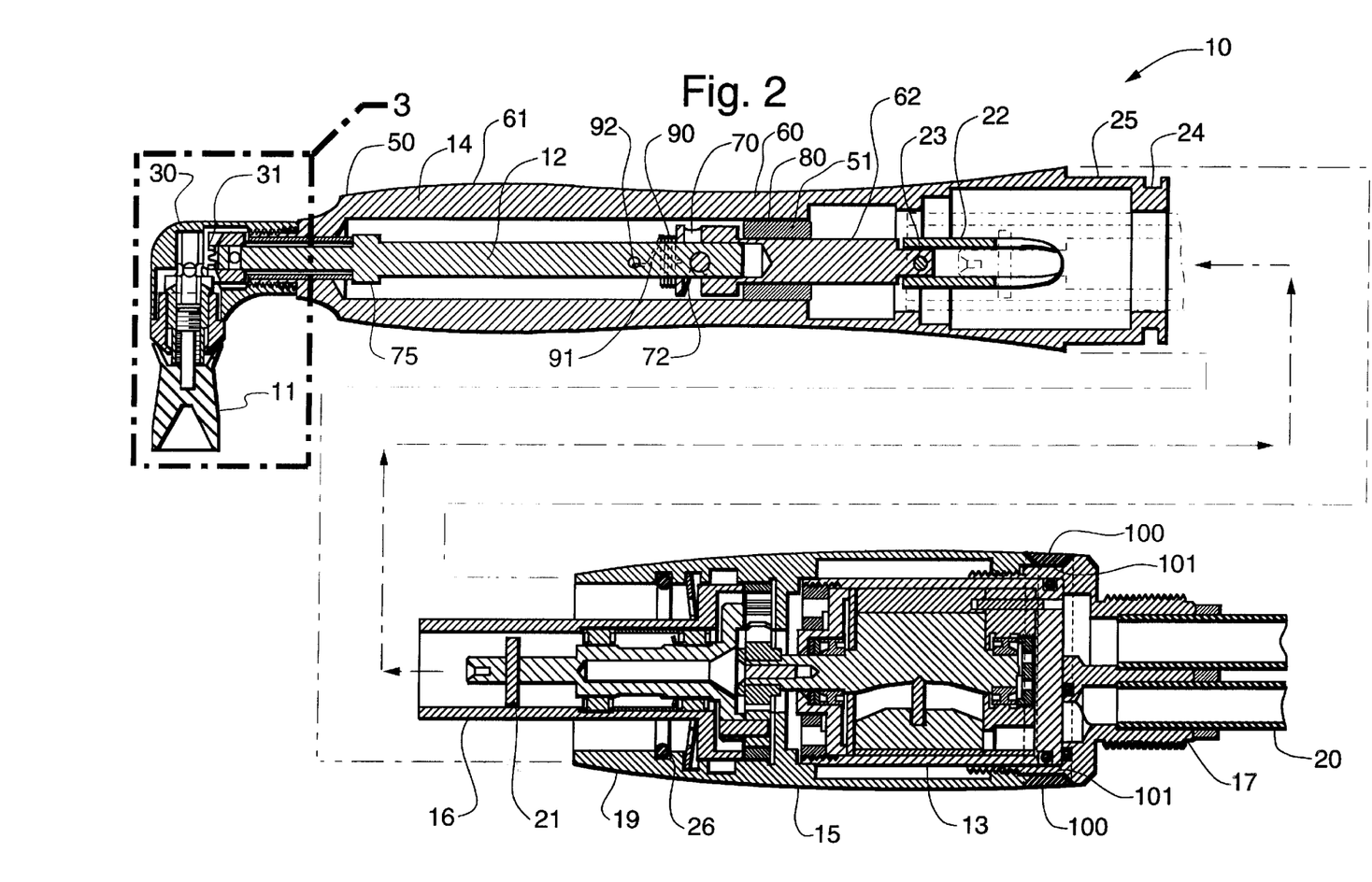
FIG. 2 is a vertical sectional view of the dental handpiece of FIG. 1, with two subassemblies shown separated for accommodating an acceptable scale.

As is conventional in the art, drive motor 13 may be housed within secondary housing 15 having a drive shaft sleeve 16 (FIGS. 2 and 5). Drive motor 13 is coupled to a power source (not shown) by use of a power source coupler 17. The source of power may be electrical energy, pressurized air (as is depicted in the drawings), pressurized fluid (including other gases or liquids) or any other conventional source without limitation. A ring seal, spacer or washer 18 may be employed between such components. Preferably, ring seal 18 is a snap ring that allows for free rotation of housing 14 with respect to secondary housing 15, although the two housing sections 14 and 15 are not disengageable due to snap ring 18.

As an example, air motor 13 is provided with pressurized air input channel 20 (FIG. 1) which transfers pressurized air to cause motor shaft 21 to rotate in a manner conventional with air motors. Channel 20a is an output or exhaust channel. Examples of other conventional motors are described for example in U.S. Pat. Nos. 4,040,311; 4,303,392; 4,260,381 and 5,569,034 which are hereby incorporated by reference for such disclosure. Drive shaft 12 is operatively connected to motor shaft 21 by any conventional means, such as coupler 22 affixed to motor shaft 21 by pin 23. Therefore, as motor shaft 21 is caused to rotate, drive shaft 12 is caused to rotate about its own axis of rotation and in the same direction as motor shaft 21 because of the operative, physical contact through coupler 22. It is not important in which direction drive motor 13 causes drive shaft 12 to rotate, except as is discussed below.

Figure 1:
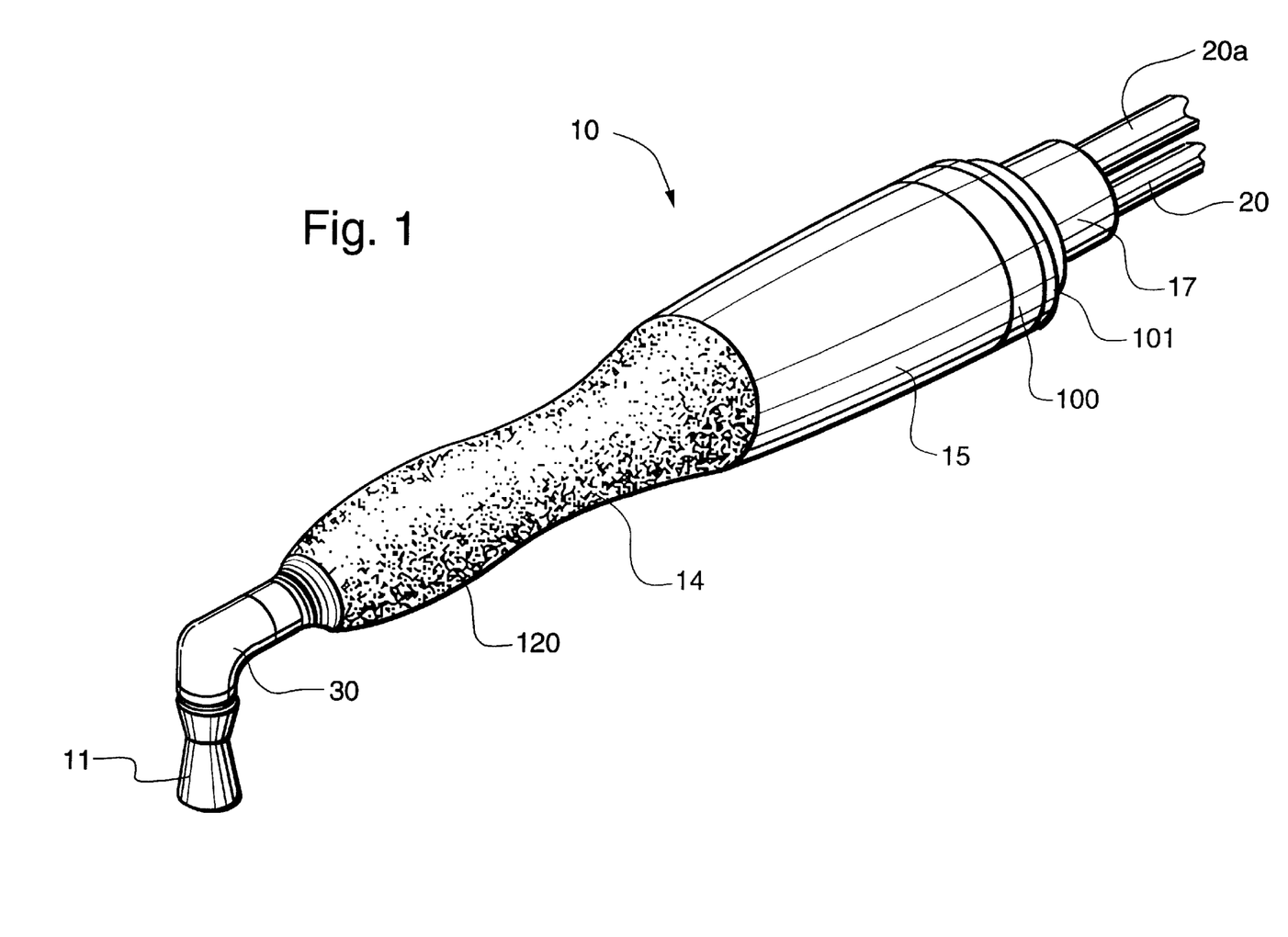
FIG. 1 is a perspective view of a dental handpiece embodying the concepts of the present invention.

Housing 14 is preferably ergonomically configured to assist the user in obtaining a firm and comfortable grip (FIG. 1). One such ergonomic configuration is shown in the drawings. As discussed above, it is also preferred that housing 14 be affixed to secondary housing 15 using snap ring 18, which is positioned within channel 24 on a connector 25 affixed to housing 14. Snap ring 18 is also positioned within channel 26 interior to secondary housing 15. By being dimensioned to protrude into each channel 24 and 26 when secondary housing receives connector 25, the two housing sections are rotatably engaged.

At the end of drive shaft 12 opposite drive motor coupler 22, the dental tool 11 is operatively affixed. One preferred means of affixing prophy cup 11 to drive shaft 12 employs angled head member 30. Angled head portions are conventional in the dental handpiece art. Drive shaft 12 is provided with mesh gear 31, and a mating mesh gear 32 (FIG. 3) is journaled within head member 30. As shaft 12 is caused to rotate, mesh gear 31 rotates in the same direction. Because of the physical contact with the mating mesh gear 32, rotational movement is translated to mating mesh gear 32 causing it to rotate as well.

Figure 4:
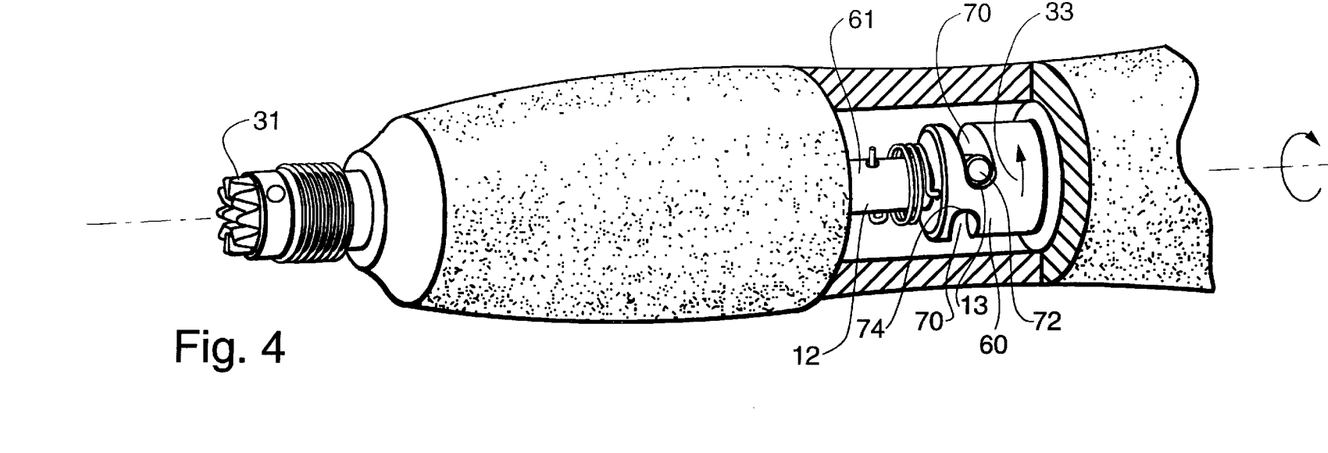
FIG. 4 is a close up, side, partially broken away view of the gripping portion of the handpiece of FIG. 1, showing a portion of the drive shaft through the broken away portion.

Dental tool 11 is preferably threadably engageable with mating mesh gear 32, such as through rotating, internally threaded coupling sleeve 40 (FIG. 3). Rotation of mating mesh gear 32 translates rotational movement to dental tool 11 through the threaded coupling sleeve 40, causing dental tool 11 to rotate as well, in a direction that is hereby termed its "normal operational direction of movement" and is exemplified by arrow 33 (FIG. 4). Coupling sleeve 40 is affixed directly or operatively affixed to mating mesh gear 32 of head 30.

Whether the thread engagement between dental tool 11 and coupling sleeve 40 is via a right or a left handed thread is not material. For simplicity, a right handed thread 41 is carried by dental tool 11, preferably upon a mounting pin 41a (FIG. 3), and a mating right handed thread 42 is carried internally by threaded sleeve 40. Thus, in use, a dental tool 11 is threaded onto handpiece 10 by mating threads 41 and 42 and then manipulating dental tool 11 to rotate in a right handed direction to engage the threads 41 and 42.

The normal operational direction of movement of dental tool 11 is opposite that which dental tool 11 is manipulated to engage threads 41 and 42. That is, with right handed threads 41 and 42, the normal operational direction of movement of dental tool 11 is the same direction as a user would manipulate dental tool 11 to disengage threads 41 and 42. In use, the dental tool 11 is pressed against a surface, such as a portion of a patient's tooth (not shown), and the friction forces generated by that physical contact are more than sufficient to prevent threads 41 and 42 from disengaging.

Drive shaft 12 is journaled within housing 14, such as by use of bearings 50 and 51 (FIG. 2) affixed within housing 14, and within which drive shaft 12 is received. Drive shaft 12 is free to rotate in either direction within bearings 50 and 51. Therefore, to remove dental tool 11 from handpiece 10, it is often difficult to simply manually rotate dental tool 11 in a direction opposite that required to mesh threads 41 and 42, that is, by manipulating or turning dental tool 11 in the same direction as its normal operational direction of movement. Because of the free rotating nature of drive shaft 12, less force is often required to rotate drive shaft 12 than is required to disengage mated threads 41 and 42. To overcome this difficulty, drive shaft 12 is provided with an axial displacement-inducing bearing 60 which will now be described.

Figure 6:
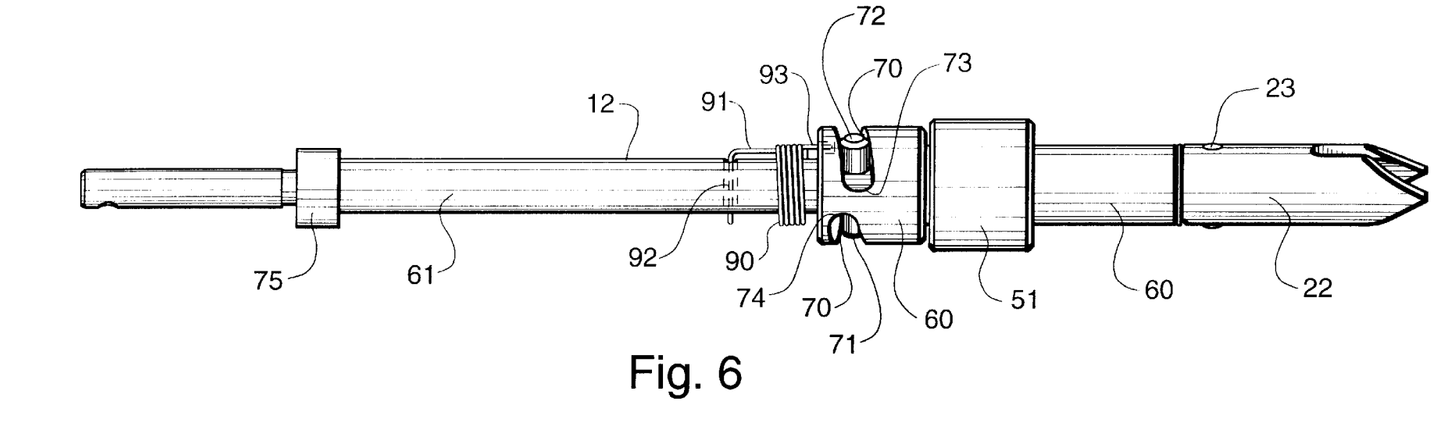
FIG. 6 is a side elevational view of the drive shaft housed internally of the handpiece of FIG. 1.

Drive shaft 12 is preferably formed by a first drive shaft section 61 and a second drive shaft section 62 (FIGS. 2 and 6). One section 61 or 62 is provided with axial displacement bearing 60. In the depiction of drive shaft 12 shown in the drawings, drive shaft section 62 carries or has affixed thereto, axial displacement bearing 60. The other section, section 61 in the drawings, is received within axial displacement bearing 60 and except for the limitations described below, is free to rotate within axial displacement bearing 60. Although it is understood that section 61 could be configured to carry axial displacement bearing 60 (this configuration not being depicted in the drawings), the invention will be exemplified as shown.

Axial displacement bearing 60 is provided with at least one and preferably two helical through slots 70. First shaft section 61 is provided with an aperture, preferably through aperture 71 at its end distal to mesh gear 31. A pin 72, is positioned within aperture 71, and is dimensioned so that when so placed, it also extends within slot 70.

A preferred configuration as shown, includes pin 72 having a length greater than the diameter of first shaft section 61, and aperture 71 being a through aperture. Further, two helical slots 70 are preferred such that one end of pin 72 extends into one slot 70 and the other end of pin 72 extends into a second slot 70.

Helical slots 70 have a first and a second end 73 and 74 respectively. As motor shaft 21 rotates, second shaft portion 62 is caused to rotate in the same direction in the manner described above. This causes axial displacement bearing 60 to rotate in the same direction because it is affixed to second shaft portion 62, as has also been described. Rotation of axial displacement bearing 60 causes first end 73 of slot 70 to physically engage one end of pin 72, forcing it to move in the same direction. Hence, rotational movement is imparted to first shaft section 61 by the physical contact between it and pin 72 through aperture 71. Rotational forces are thereby translated to dental tool 11 in the manner above described.

Helical slots 70 are also preferably configured to rise in a direction similar to that of the direction that imparts rotational movement to dental tool 11 to rotate in its normal operational direction of movement. That is, in use, if shaft 12 rotates to the right (that is, the direction of arrow 33) it is preferred that helical slots 70 rise to the right about the shaft 12 rotational axis. It will be appreciated therefore, that when it is desired to remove dental tool 11 from handpiece 10, a user will manipulate dental tool 11 to rotate in a direction the same as the normal operational direction of movement. This will tend to cause first shaft section 61 to rotate within axial displacement bearing 60 (in the direction shown by arrow 33), thereby causing pin 72 to rise within helical slot 70. This movement of pin 72 causes first shaft section 61 to be axially displaced, or moved away from, second shaft section 62, because pin 72 is in physical contact with first shaft section 61 by aperture 71. The shaft 12 in a sense, becomes longer because pin 72 is rising within helical slot 70 with which pin 72 is in physical contact.

When first and second shaft sections 61 and 62 are axially displaced by the rising of pin 72 within helical slot 70, axial displacement bearing 60 is caused to physically engage or rub against bearing 51. At the other end of first shaft section 61, a hub 75 is affixed. As first shaft section 61 is displaced from second shaft section 62, hub 75 is caused to physically engage or rub against, bearing 50. The physical contact between hub 75 and bearing 50, and the physical contact between axial displacement bearing 60 and bearing 51, causes shaft 12 to bind due to the frictional forces caused by the two physical engagements. The frictional forces increase until they are greater than the force required to disengage mating threads 41 and 42, permitting their complete disengagement and hence, removal of dental tool 11. Open area 80 may be provided to allow longitudinal movement of shaft 12 as pin 72 moves and rises within slots 70.

To prevent undue wear, it is desired to return pin 72 into physical engagement with first end 73 of slot 70 after disengagement of threads 41 and 42. One preferred means of accomplishing this is to provide a spring bias means such as coil spring 90 wrapped around first shaft section 61 (FIGS. 2 and 6). Coil spring 90 has one free end 91 physically engaged with first shaft section 61, such as by being inserted into a second aperture 92, and a second free end 93 physically engage with second shaft section 62 such as by being affixed to axial displacement bearing 60. Thus, as dental tool 11 is caused to be manipulated (such as by being grasped and manually rotated, this not being shown but understood) in a direction the same as its normal operational direction of movement, and axial displacement of shaft sections 61 and 62 relative to each other to disengage threads 41 and 42, coil spring 90 is caused to compress. When manipulative forces are removed, that is, when dental tool 11 is removed, coil spring 90 will bias first section 61 in a direction opposite that of second section 62, causing shaft sections 61 and 62 to displace in a direction toward each other.

The aspect of the invention to allow efficient removal of dental tool 11 from handpiece 10 serves to improve the overall hygienic nature of the invention. Because of the ease of maintenance afforded, quick and numerous dental tool 11 changes will be encouraged. To further the hygienic nature of handpiece 10, it is an aspect of the invention to provide for quick and easy visual determination of one handpiece 10 as compared to another. This is useful for example, in determining which handpiece 10 is to be employed as between those of multiple users, multiple patients, multiple handpieces and the like.

The visual distinguishing character of the invention is provided by an elastic band 100 (FIG. 2) positioned within a band channel 101. Band channel 101 can be located at any point along the body of handpiece 10, as is shown on the drawings in one preferred location proximate to motor drive unit 13. Band 100 preferably fits within channel 101 so as to be flush with the physically adjacent surfaces of handpiece 10. By providing color bands 100 of different colors, a specific color band can be assigned to a specific user or to a specific task. Hence, the handpiece 10 to which the color band 100 is affixed is dedicated to that user or task and is easily distinguished from other handpieces having a different color band.

It will be appreciated that channel 101 need not be completely circumferential, and that band 100 need not be continuous. Band 100 might be a medallion or other identifying article or device (not shown), and channel 101 need only be an indentation to receive the band 100 or such other device. All such variations fall within the scope of the invention.

It is another aspect of the invention to provide for improved cleaning capabilites of angled head portion 30. Head portion 30 is provided with spindle 110 which spindle 110 is received within threaded sleeve 40. Such a configuration is conventional in the art. However, spindle 110 is normally a solid pin or axle. According to the present invention, spindle 110 is hollow and is provided with cross-slots 111. It will be appreciated that when head portion 30 is removed from handpiece 10, and placed in a conventional steam cleaner, steam is free to enter cross-slots 111, travel through the interior of hollow spindle 110 and into the internal portions of threaded sleeve 40. This improvement enhances and quickens the cleaning of angled head portion 30.

As stated above, housing 14 is contoured to provide an efficient grasping surface for the user. In one preferred configuration, housing 14 is configured to be flush with secondary housing 15. To provide an even more secure grip, housing 14 may be provided with a roughened exterior by any conventional means.

As shown in FIG. 1, the roughened exterior surface of housing 14 is provided as a plurality of spherical indentations 120 thereon. While any means of providing a roughened surface within the scope of the invention, it is preferred to contact the surface housing 14 with a plurality of high velocity spherical balls, which will make corresponding spherical indentations 120.

It is evident therefore, that the objects of a dental handpiece are carried out by the invention as herein described. All possible aspects of the invention beyond the best mode have not been necessarily described, and the scope of the invention shall only be determined by the following claims.

I claim:

1. A dental handpiece comprising:

a housing;

a head portion affixed to said housing;

a rotatable drive shaft journaled within said housing, and having a first and a second cooperating section and an axis of rotation;

a rotatable dental tool operatively connected to said first section of said drive shaft;

drive motor means operatively connected to said second section of said drive shaft to selectively and rotatably drive said drive shaft about its axis of rotation;

means to couple said first and second drive shaft sections, comprising an axial displacement bearing affixed to one of said sections and receiving the other said section;

said axial displacement bearing having at least one helical slot therein;

a pin affixed to said shaft section received within said axial displacement bearing and said pin positioned within said helical slot so as to be in operative, physical contact with said axial displacement bearing;

such that as said drive motor means causes said second section of said drive shaft to rotate, first section of said drive shaft by said pin being in said physical contact with said axial displacement bearing helical slot, thereby causing a rotational force to be applied to said dental tool and causing its rotation.

2. A handpiece as in claim 1, wherein said operative connection between said drive shaft and said dental tool includes at least one drive gear, such that rotation of said drive shaft causes said drive gear to rotatably drive said dental tool.

3. A handpiece as in claim 2, wherein said operative connection between said drive shaft and said dental tool further includes helical thread means; and wherein manual rotation of said dental tool causes rotation of said thread means, thereby rotating said drive shaft and causing said pin to move within said helical slot.

4. A handpiece as in claim 3, further comprising a spring bias means in physical engagement at one end with said drive shaft section journaled within said axial displacement bearing, and at its other end with said axial displacement bearing, such that manually turning said dental tool thereby rotating said drive shaft, causes said spring means to compress, thereby biasing said drive shaft section journaled within said axial displacement bearing in an opposite direction.

5. A dental handpiece of the type having a drive motor unit rotatably driving a drive shaft journaled within a housing portion of said handpiece, and a dental tool affixed to said drive shaft, wherein rotation of said drive shaft causes said dental tool to rotate; the improvement comprising:

said drive shaft comprising a first drive shaft section and a second drive shaft section; said dental tool operatively affixed to said first drive shaft section and said drive motor unit operatively affixed to said second drive shaft section; said second drive shaft section having an affixed axial displacement bearing receiving at least a portion of said first drive shaft section; said axial displacement bearing having at least one helical slot therein, said helical slot rising in the same direction as the normal operational direction of rotation as said drive shaft; a pin affixed to said first shaft section received within said axial displacement bearing and positioned within said at least one helical slot; such that manipulation of said dental tool in its normal operational direction of movement causes said first drive shaft section received within said axial displacement bearing to rotate in its normal operational direction of movement, thereby causing said pin to rise within said helical slot, causing the said first drive shaft section to be axially displaced from said second drive shaft section.

6. A dental handpiece as in claim 5, further comprising at least one additional bearing within said housing and within which said shaft is received.

7. A dental tool as in claim 6, wherein said at least one additional bearing is positioned in juxtaposition with said axial displacement bearing, such that as said first and second shaft sections are axially displaced, said axial displacement bearing is caused to physically engage said at least one additional bearing.

8. A dental tool as in claim 7, wherein said first drive shaft section is provided with a circumferential hub, and a second bearing is affixed within said housing proximate to said hub when said shaft is received within said housing; such that said axial displacement of said first and second shaft sections causes hub to physically engage said second bearing.

9. A handpiece as in claim 5, wherein the improvement further comprises a spring bias means affixed to said shaft which said spring bias means compresses or expands when said dental tool is manipulated in its normal operational direction of movement, biasing said drive shaft.

10. A dental handpiece comprising:

a drive motor;

a drive shaft having a first and a second shaft section, said second shaft section operatively affixed to said drive motor;

a dental tool operatively affixed at one end of said first shaft section;

said first shaft section being journaled within an axial displacement bearing means, such that manipulated rotation of said dental tool causes said first and second drive shaft sections to be axially displaced from one another, wherein said axial displacement bearing means includes a helical slot within said axial displacement bearing means, and a pin positioned within an aperture within said first drive shaft and extending into said helical slot.

11. A dental tool as in claim 10, wherein said drive motor is operatively affixed to said axial displacement bearing means, such that said axial displacement bearing means is rotatably driven by said drive motor, and said pin is physically engaged with said axial displacement bearing means by being positioned within said helical slot, such that said pin is caused to rotate in the same direction, thereby causing said drive shaft to rotate in the same direction.

12. A dental tool as in claim 11 wherein manipulation of said dental tool in the same direction in which said drive motor operatively rotates said dental tool, causes said pin to rise within said helical slot, such that said first and second shaft sections are axially displaced.

* * * * *

UNITED STATES PATENT AND TRADEMARK OFFICE
CERTIFICATE OF CORRECTION

PATENT NO. : 6,012,922
DATED : January 11, 2000
INVENTOR(S) : Eugene J. Novak

It is certified that error appears in the above-identified patent and that said Letters Patent is hereby corrected as shown below:

Claim 1, column 8, line 11, insert --a rotating force is translated to said-- immediately following the phrase "section of said drive shaft to rotate,".

Signed and Sealed this

Twenty-sixth Day of December, 2000

*Attest:*

Q. TODD DICKINSON

*Attesting Officer*    *Director of Patents and Trademarks*